(12) United States Patent
Anderson et al.

(10) Patent No.: US 9,517,021 B2
(45) Date of Patent: Dec. 13, 2016

(54) COMMUNICATING BETWEEN MRI CONTROL SYSTEM AND RF COILS

(71) Applicant: Toshiba Medical Systems Corporation, Otawara-Shi, Tochigi (JP)

(72) Inventors: Robert Anderson, Mayfield Heights, OH (US); Yoshinori Hamamura, Moreland Hills, OH (US)

(73) Assignee: TOSHIBA MEDICAL SYSTEMS CORPORATION, Otawara-Shi, Tochigi-Ken (JP)

( * ) Notice: Subject to any disclaimer, the term of this patent is extended or adjusted under 35 U.S.C. 154(b) by 312 days.

(21) Appl. No.: 14/033,767

(22) Filed: Sep. 23, 2013

(65) Prior Publication Data

US 2015/0087966 A1    Mar. 26, 2015

(51) Int. Cl.
*A61B 5/055* (2006.01)
*A61B 5/00* (2006.01)

(52) U.S. Cl.
CPC ........... *A61B 5/0555* (2013.01); *A61B 5/0002* (2013.01)

(58) Field of Classification Search
CPC combination set(s) only.
See application file for complete search history.

(56) References Cited

U.S. PATENT DOCUMENTS

| 5,206,946 | A | * | 4/1993 | Brunk | H03M 9/00 710/2 |
| 6,650,926 | B1 | * | 11/2003 | Chan et al. | 600/422 |
| 7,391,214 | B2 | | 6/2008 | Adachi | |
| 8,275,318 | B2 | * | 9/2012 | Hoyt | H04B 5/02 310/268 |
| 8,909,320 | B2 | * | 12/2014 | Jenkins | 5/600 |
| 2003/0206019 | A1 | | 11/2003 | Boskamp | |
| 2008/0238625 | A1 | * | 10/2008 | Rofougaran | H04B 5/0012 340/10.1 |
| 2011/0137144 | A1 | * | 6/2011 | Rofougaran et al. | 600/407 |

OTHER PUBLICATIONS

TransferJet™ Overview, Concept and Technology, Rev. 1.1, Feb. 2010, TransferJet Consortium, copyright 2010.
System Description Wireless Power Transfer, vol. 1: Low Power, Part 1: Interface Definition, Version 1.0.3, Sep. 2011, Wireless Power Consortium, copyright 2011.

* cited by examiner

*Primary Examiner* — Katherine Fernandez
*Assistant Examiner* — Farshad Negarestan
(74) *Attorney, Agent, or Firm* — Nixon & Vanderhye P.C.

(57) ABSTRACT

A magnetic resonance imaging (MRI) system, method and/or apparatus is configured to effect MR imaging where data corresponding to MR signals is transmitted from a radio frequency (RF) receive coil to the MRI data processor via a path that includes a near-field wireless communication (NFC) connection. A receiver for the NFC connection is selected from of the one or more wireless signal receivers that are arranged on a restraining belt when the restraining belt is placed, during operation of an MRI system for imaging an object located on a patient table, over at least a portion of the object and the receive RF coil is located between the restraining belt and the object.

20 Claims, 7 Drawing Sheets

COMMUNICATING BETWEEN MRI CONTROL SYSTEM AND RF COILS

FIELD

The subject matter below relates generally to magnetic resonance imaging (MRI), and more particularly systems, methods, and apparatuses for arranging radio frequency (RF) coils and the connection between the RF coils and the MRI data processing system.

DETAILED DESCRIPTION

Figure 1:
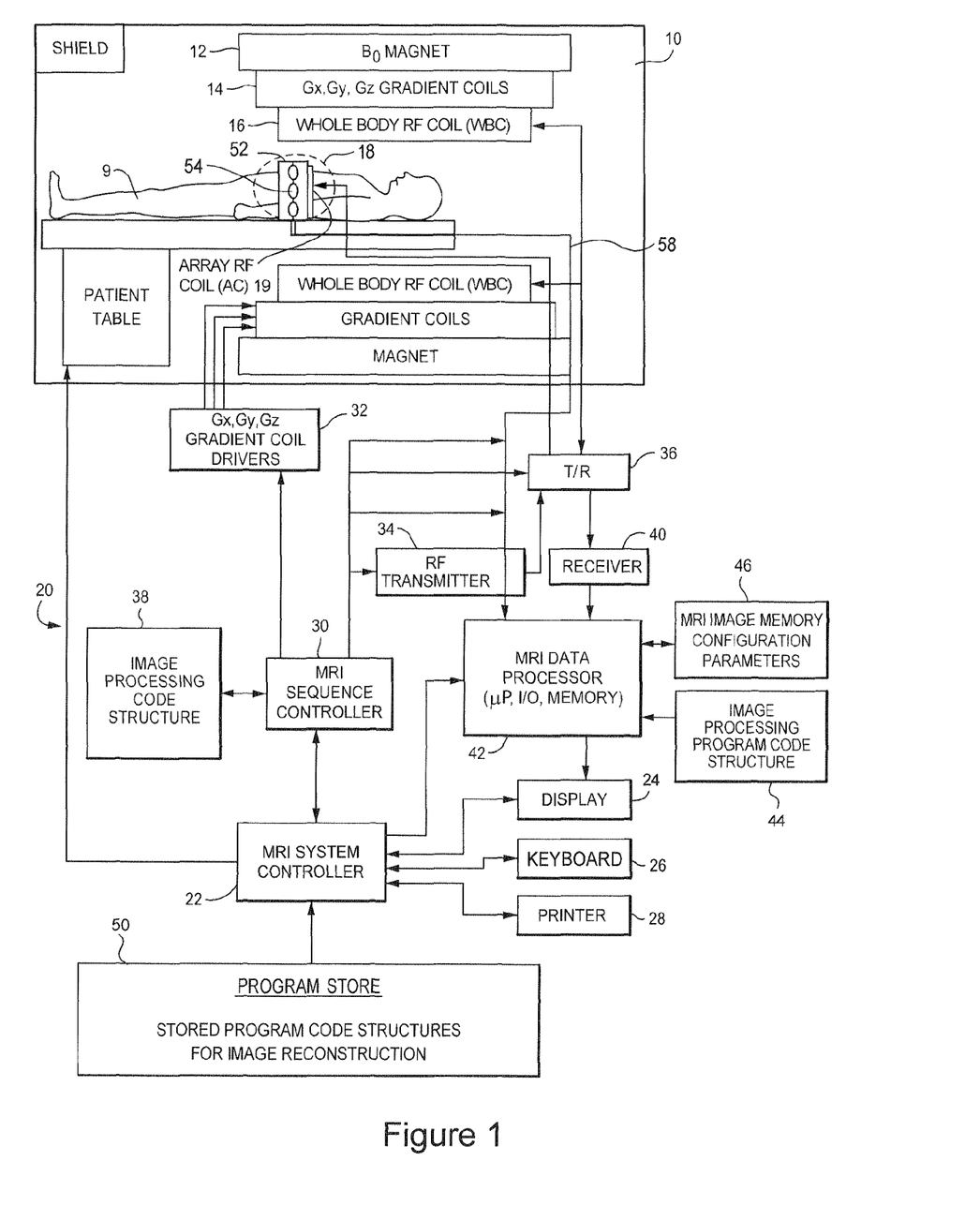
FIG. 1 is a high-level schematic block diagram of an MRI system adapted to incorporate wireless antenna in a restraining belt (e.g., patient immobilizing belt) attached to the patient table of the MRI system, in accordance with one or more embodiments.

The MRI system shown in FIG. 1 includes a gantry 10 (shown in schematic cross-section) and various related system components 20 interfaced therewith. At least the gantry 10 is typically located in a shielded room. The MRI system geometry depicted in FIG. 1 includes a substantially coaxial cylindrical arrangement of the static field B0 magnet 12, a Gx, Gy and Gz gradient coil set 14 and a large whole body radio frequency (RF) coil (WBC) assembly 16. Along the horizontal axis of this cylindrical array of elements is an imaging volume 18 shown as substantially encompassing a portion of the upper body of patient 9 supported by a patient table 11. A restraining belt (sometimes referred to as a "patient immobilizing belt") 52 is positioned such that it restrains patient 9 to patient table 11. A smaller array RF coil (AC) 19 might be more closely coupled to a portion of the patient that is at least partly under restraining belt 52. The part of patient 9 that is subject to scanning using RF coil 19 is referred to herein, for example, as "scanned object" or "object" in imaging volume 18. As those in the art will appreciate, compared to the WBC (whole body coil), relatively small coils and/or arrays such as surface coils or the like are often customized for particular body parts (e.g., arms, shoulders, elbows, wrists, knees, legs, chest, spine, etc.). Such smaller RF coils are herein referred to as array coils (AC) or phased array coils (PAC). These may include at least one coil configured to transmit RF signals into the imaging volume and one or more receiver coils configured to receive RF signals from an object, such as the part of the patient upper body in the example above, in the imaging volume.

Restraining belt 52 includes one or a plurality of wireless signal receivers and/or transceivers (control-side wireless antenna) 54 that are connected via one or more wires 58 to MRI data processor 42 for communicating between RF coil 19 and MRI data processor 42. During operation of the MRI system for scanning, one or more of the control-side wireless antenna 54 establishes a connection with a corresponding wireless signal transmitter and/or transceiver (coil-side wireless antenna, not shown in FIG. 1) which is physically coupled to RF coil 19.

An MRI system controller 22 has input/output ports connected to a display 24, keyboard 26 and printer 28. As will be appreciated, the display 24 may be of the touch-screen variety so that it provides control inputs as well.

The MRI system controller 22 interfaces with MRI sequence controller 30 which, in turn, controls the Gx, Gy and Gz gradient coil drivers 32, as well as the RF transmitter 34 and the transmit/receive switch 36 (if the same RF coil is used for both transmission and reception). The MRI sequence controller 30 includes suitable program code structure 38 for implementing MRI imaging (also known as nuclear magnetic resonance, or NMR, imaging) techniques. The MRI imaging techniques may include, for example, parallel imaging and/or other imaging sequences.

The MRI system 20 includes an RF receiver 40 providing input to data processor 42 so as to create processed image data, which is sent to display 24. The MRI data processor 42 is also configured for access to system configuration parameters 46 and MRI image reconstruction program code structures 44 and 50. MRI image reconstruction program code structures 44 and 50 may, in addition to control logic for reconstructing MRI images, also include control logic to obtain MR data from RF coils 16 and/or 19.

Although shown in FIG. 1 as being located away from the RF coils 16 and 19, in some embodiments, any of RF transmitter 34, transmit/receive switch 36, and RF receiver 40 may be located in close proximity to, or on a surface of, either or both RF coils 16 and 19.

Also illustrated in FIG. 1 is a generalized depiction of an MRI system program store 50 where stored program code structures (e.g., for image reconstruction, for defining graphical user interfaces and accepting operator inputs to same, etc.) are stored in non-transitory computer-readable storage media accessible to the various data processing components of the MRI system. As those in the art will appreciate, the program store 50 may be segmented and directly connected, at least in part, to different ones of the system 20 processing computers having most immediate need for such stored program code structures in their normal operation (i.e., rather than being commonly stored and connected directly to the MRI system controller 22)

Indeed, as those in the art will appreciate, the FIG. 1 depiction is a very high-level simplified diagram of a typical MRI system with some modifications so as to practice exemplary embodiments described hereinbelow. The system components can be divided into different logical collections of "boxes" and typically comprise numerous digital signal processors (DSP), microprocessors and special purpose processing circuits (e.g., for fast A/D conversions, fast Fourier transforming, array processing, etc.). Each of those processors is typically a clocked "state machine" wherein the physical data processing circuits progress from one physical state to another upon the occurrence of each clock cycle (or predetermined number of clock cycles).

Not only does the physical state of processing circuits (e.g., CPUs, registers, buffers, arithmetic units, etc.) progressively change from one clock cycle to another during the course of operation, the physical state of associated data storage media (e.g., bit storage sites in magnetic storage media) is transformed from one state to another during operation of such a system. For example, at the conclusion of an image reconstruction process and/or sometimes a coil sensitivity map generation process, an array of computer-readable accessible data value storage sites in physical storage media will be transformed from some prior state (e.g., all uniform "zero" values or all "one" values) to a new state wherein the physical states at the physical sites of such an array vary between minimum and maximum values to represent real world physical events and conditions (e.g., the internal physical structures of a patient over an imaging volume space). As those in the art will appreciate, such arrays of stored data values represent and also constitute a physical structure—as does a particular structure of computer control program codes that, when sequentially loaded into instruction registers and executed by one or more CPUs of the MRI system 20, causes a particular sequence of operational states to occur and be transitioned through within the MRI system.

The exemplary embodiments described below provide improved ways to communicate between RF coils and the control system. In particular, exemplary embodiments may improve patient safety and coil placement flexibility when acquiring MRI images.

During the scanning process, with the patient located in the MRI gantry, one or more RF coils, such as whole body coil 16 and/or array coil 19, may transmit RF pulses to selected parts of the patient in order to excite nuclear spin in particular parts of the patient's body. For example, whole body coil 16, which is placed in the magnet gantry, may be used to excite nuclear spin specifically in that area. Subsequently, MR signals (e.g., echo signals) which are generated as a result of the earlier excitation are received by one or more receive RF coils. The transmitting of the RF pulses and the receiving of the MR signals may be by the same RF coil (e.g., RF coil 16 configured for both transmit RF excitation pulses and receive corresponding MR signals) or by different RF coils (e.g., WBC 16 is configured to transmit RF pulses and RF coil 19 is configured to receive corresponding MR signals). In order to generate MRI images for diagnostic or other purposes, data corresponding to the MR signals must be communicated to a control system, such as, for example, a processing system including MRI data processor 42, for processing. The data corresponding to MR signals may be referred to as "MR signal data" and represents the digitized MR signal.

The amount of MR signal data that is acquired during a scanning iteration can be large. In order to satisfy the relatively high data rate requirements and reliability requirements in transferring MR signal data, most of the distance in the path from the RF coils to the data processing system is usually by wire or optical fiber.

However, wire from the receive RF coil(s) to the control system may significantly restrict available options for patient and/or coil placement. For example, any wire that is close to the patient may pose a burn risk, either due to making contact with the patient and/or due to being in the way of high RF fields generated when excitation pulses are transmitted. RF energy associated with RF pulses induced on a patient and the RF coil wire can heat up the patient tissue to cause damage when it is not setup appropriately. Moreover, options for placing RF coils upon the patient may be restricted because of requirements regarding patient safety due to possible interference of the wire with patient movement and the like. Similar concerns may exist even when the data from a receive RF coil is transmitted wirelessly from a wireless signal transmitter attached by wire to a receive RF coil, because the wire from the RF coil may have to be extended to a location on the patient table so that a wireless connection can be established between the wireless signal transmitter and a wireless signal receiver fixed to the patient table.

The embodiments described herein utilize wireless communication in order to improve patient safety, availability of coil placement choices and the efficiency of the scanning process. Patient safety is improved by reducing the risk of burn that may occur due to exposed wire. For example, the wireless signal transmitter is directly or at least very closely attached to a surface of the receive RF coil, thereby entirely or substantially eliminating risk due to exposed wire between the receive RF coil and attached wireless signal transmitter. Moreover, in order to enable the shortening or eliminating of the wire from the RF coil to the wireless signal transmitter, a plurality of wireless signal receivers are flexibly arranged such that wireless connections can be established without extending the wireless signal transmitters away from the RF coil to which they are attached, thereby reducing the amount of exposed wire. Coil placement choices are improved by enabling connections between wireless signal transmitters and receivers at any location at which a restraining belt can be disposed. Moreover, at least in some embodiments, the requirement for manually connecting the wire from the RF coils to cabling that extends to the MRI control system is eliminated or reduced, thereby improving the efficiency of the scan process.

Figure 2A:
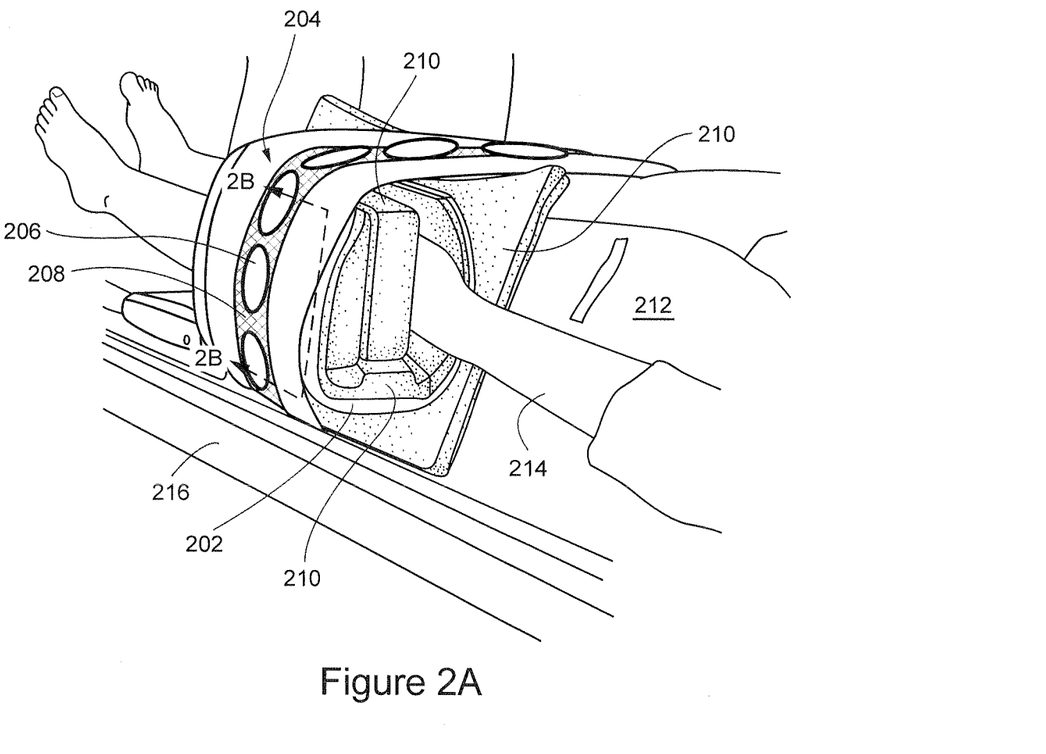
FIG. 2A illustrates an example sketch of an arm of a patient and a RF coil secured to a patient table of an MRI system using a restraining belt that has incorporated wireless antenna for receiving data corresponding to magnetic resonance (MR) signals, in accordance with one or more embodiments.

FIG. 2A illustrates an example sketch of an arm 214 of a patient 212 secured to a patient table 216 of an MRI system using a restraining belt 204 that has incorporated wireless antenna 208 for receiving MR signal data, in accordance with one or more embodiments. Between restraining belt 204 and arm 214 is an RF coil 202. Padding 210 may be placed in various locations, such as between RF coil 202 and arm 214 and/or between RF coil 202 and rest of the body of patient 212. Restraining belt 204 may correspond to restraining belt 52, and RF coil 202 may correspond to RF coil 19 shown in FIG. 1.

Padding 210 may be used for improved positioning of the patient and/or RF coil, and also for preventing direct contact between the patient and RF coil 202. Padding may be formed using polyurethane, foam, or like material.

RF coil 202 may be an array or surface RF coil which is specifically designed for scanning areas such as the arm. In other embodiments, RF coil 202 may be a coil designed for scanning any other part of the body, but which is being used for scanning an arm. In some embodiments, RF coil 202 may comprise more than one coil (e.g., separate posterior coil and anterior coils). RF coil 202 has one or more wireless signal transmitters (not shown) positioned on its outer-side. For example, one or more wireless signal transmitters can be positioned between coil 202 and restraining belt 204. The transmitter(s) can be attached, either directly or via very short wire, to coil 202 in a manner that the wire does not pose any burn risk to the patient. For example, in one embodiment, wireless signal transmitters are attached onto the outer surface of the coil, whereas in another embodiment, they are attached with short wire to some location on RF coil 202. A person of skill in the art will understand that the wireless signal transmitters may not necessarily be attached to the physical coil element of RF coil 202, and is generally attached to a cover or some other structure that contains the physical coil elements that receive RF signals.

In addition to the wireless signal transmitter, RF coil 202 may also have incorporated other components such as an analog/digital converter, parallel to serial converter, modulator and the like which may be required for converting the received RF MR signals to digitized MR signal data which can be transmitted. Moreover, RF coil 202 may include a rechargeable battery (not shown) or power receiver (not shown) to provide power. Recharging of the battery and/or supplying power to the power receiver may be performed using any known technique, such as, for example, wireless electrical charging.

According to some embodiments, RF coil 202 is wirelessly provided a reference signal (e.g., sampling clock), and trigger to start/stop analog to digital conversion. For example, control-side wireless antennae 206 of the restraining belt may include, in addition to wireless signal receivers, one or more wireless signal transmitters. Correspondingly, coil-side wireless antenna may, in addition to the wireless signal transmitters, include one or more wireless signal receivers. Note that when both a transmitter and a receiver antenna are on the coil-side and on the control side, separate wireless connections may be formed between each transmitter receiver pairing. For example, two separate wireless connections may be formed for each pair of communicating coil-side wireless antennae 220 and control-side wireless antennae 206. Information such as the reference clock, analog digital trigger and other control and/or configuration information for RF coil 202 may be communicated from, for example, MRI sequence controller 30.

Restraining belt 204 may be used to hold the patient or a part of the patient in a substantially immovable position in relation to patient table 216. Restraining belts are available in many MRI systems to ensure that the patient does not move during the scan. As shown, in embodiments, restraining belt 204 is adapted by incorporating a plurality of wireless antenna 206.

The plurality of near field wireless communication (NFC) antennae 206 may be arranged on either the outer or inner surface of restraining belt 204. In some embodiments, antennae 206 may be incorporated into restraining belt 204, e.g., in between the outer surface and the inner surface. The plurality of antennae 206 may be arranged in a configured layout according to any pattern. The layout (e.g., spatial arrangement) of the antennae 206 may be such that, either along substantially the entire length of the restraining belt or in selected local areas, wireless antennae 206 of the restraining belt are arranged so that they have a higher density than the density with which wireless antennae (not shown) are arranged on RF coils 202 placed between restraining belt 204 and patient arm 214. Having wireless receive antennae 206 arranged with a higher density than transmitters improves the flexibility afforded for coil placement, so that, for example, fine positioning adjustments can be made to coil position in order to obtain an optimal image without worrying about alignment between transmitters and receive antennae.

The plurality of wireless antennae 206 may be arranged along the length of the outer surface of restraining belt 204 as, for example, shown in FIG. 2A. The plurality of wireless antennae 206 may be connected via wire 208 to a data processing system, such as, for example, MRI data processor 42 shown in FIG. 1.

Restraining belt 204 is configured to be attached to patient table 216, and may be either detachably or permanently attached to the patient table. The attachment to patient table 216 may be at the side edges of table 216. In some embodiments, restraining belt 204, or the attachment point(s) of restraining belt 204 to patient table 216, is fixed in position relative to patient table 216. In another embodiment, the attachment point of restraining belt 204 is movable (e.g., slidable) across the corresponding side of the table. In effect, the point at which restraining belt 204 restrains the patient may be changed by moving restraining belt 204 (and/or its attachment point) along the side of the patient table.

Communication wire(s) 208, which is (are) arranged upon a surface of restraining belt 204 or incorporated into restraining belt 204, may comprise one or more individual data communications wires. According to an embodiment, wire 208 includes at least one respective wire for each of the plurality of wireless antennae 206 arranged on restraining belt 204. According to another embodiment, respective wires may be configured to be accessed by more than one of the wireless antennae 206. Appropriate shielding etc. may be provided for wire(s) 208.

In another embodiment, one or more controllers (e.g., for protocol conversion) may be incorporated into wire(s) 208. Wire(s) 208 either continue or connect to other data transmission cable(s) at edges of the patient table, so that MR signals or data corresponding to the MR signals are sent to the MRI data processor.

Figure 2B:
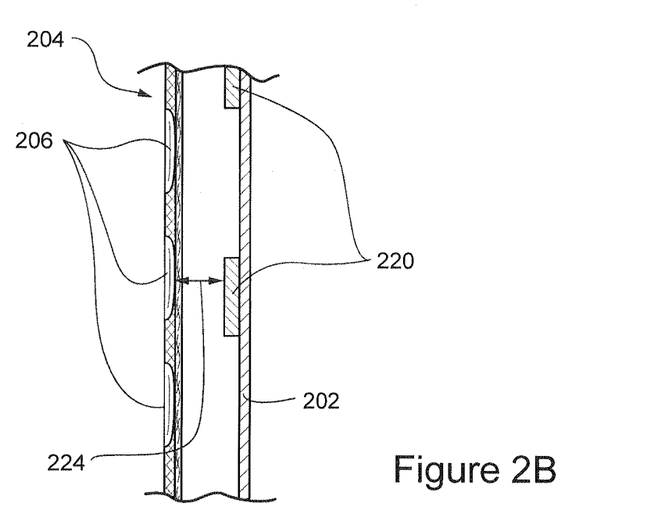
FIG. 2B illustrates a sketch of a part of the RF coil with a part of the restraining belt is disposed over it, in accordance with one or more embodiments.

FIG. 2B illustrates an example close-up sketch in an area where contact or near contact between a wireless signal transmitter 220 and receiver 206 is established in the arrangement shown in FIG. 2A. In the illustrated area, three wireless signal receivers 206 of restraining belt 204 are shown in close proximity to RF coil 202 with two wireless signal transmitters 220 shown as attached to the outer surface of the RF coil. As shown in FIG. 2B, transmitters 220 are arranged with lower spatial density (e.g., with more distance between two transmitters) when compared to the receivers 206. In the illustrated scenario, a wireless connection may be best established over the space 224 between the illustrated middle receiver 206 and the nearest (lower as illustrated) transmitter 220.

In embodiments, the wireless signal antennae receivers and wireless signal transmitters support wireless connections between entities that are in close proximity to each other. A near-field wireless communication (NEC) protocol used in some example embodiments requires that the separation of the corresponding transmitter/receiver pair be no more than a few centimeters or less (e.g., 2 centimeters) apart. The use of NFC for the wireless connection in embodiments, because of the very small distance between the transmitter and receiver, ensures that many of the problems related to power, reliability, interference, security, and the like, associated with many other wireless connection techniques are not present in embodiments. An example NFC connection is described below in relation to FIG. 6.

The number of wireless antennae 206 and/or transmitters 220 may be determined based upon considerations such as, for example, data transfer rate to be supported, size of coil, number of channels in an RF coil, desired flexibility in coil and/or patient positioning, location of restraining belt, and transfer rate of the data transfer protocol. In some embodiments, for example, a 16 channel RF coil requires at least two connections, each connection requiring a coupling between a coil-side wireless transmit antenna and a control-side wireless receive antenna, in order to accommodate an imaging data rate of 32 Mbps per channel when the transfer protocol has a transfer rate of 375 Mbs (e.g., one pairing of coil-side and control-side antennas for each 11 channels).

Co-pending U.S. patent application Ser. No. 13/945,370 filed on Jul. 18, 2013, which is hereby incorporated by reference in its entirety, further describes example wireless signal receivers and wireless signal transmitters which can be used for the NFC connection.

Figure 3:
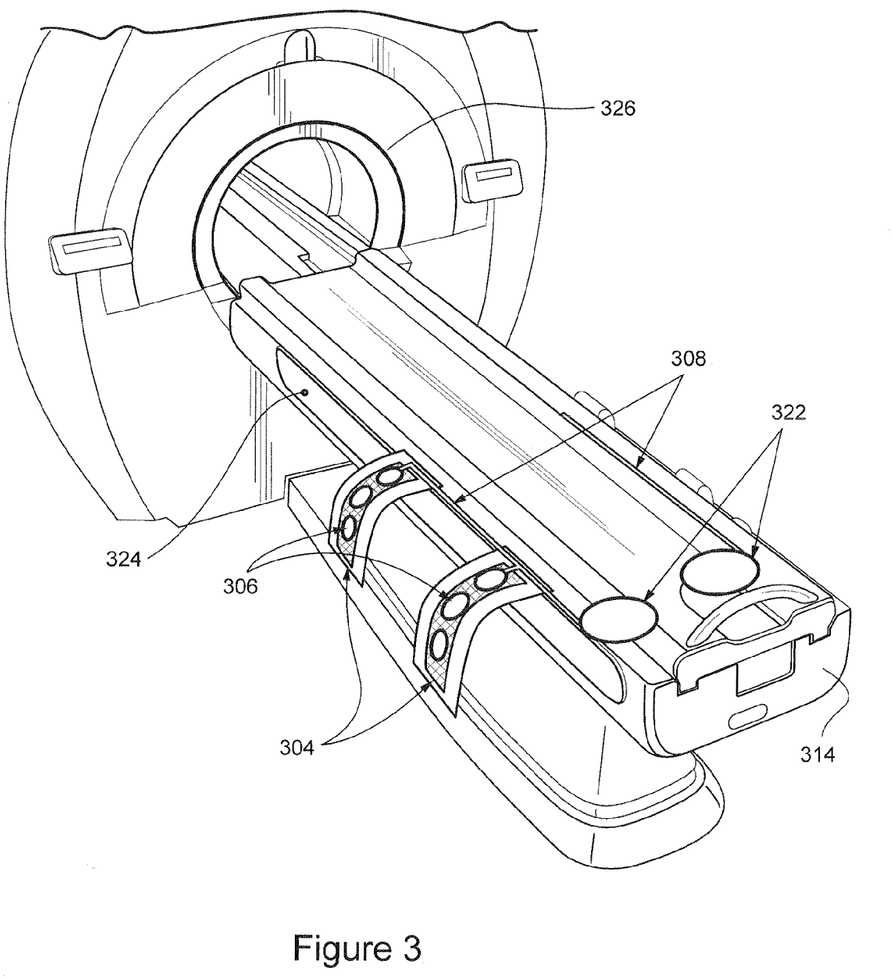
FIG. 3 illustrates a sketch of an example patient table, in accordance with one or more embodiments.

FIG. 3 illustrates an example patient table 314, in accordance with one or more embodiments. Patient table 314 may correspond to patient tables 216 in FIG. 2A and patient table 11 in FIG. 1. Patient table 314 is configured to be movable in and out of MRI gantry 326. For example, a patient may be prepared for scanning by positioning her on table 314, while table 314 is completely or partially outside of MRI gantry 326. Preparing the patient may include, for example, positioning the patient on table 314, placing one or more RF coils at selected locations of the patient, and securing the patient to the table using one or more restraining belts 304. After the preparation is complete, table 314, with the patient substantially immovably being positioned on table 314, is moved into gantry 326 where the scanning takes place.

Attached to patient table 314 are two restraining belts 304 that have incorporated in each a plurality of wireless antennae 306. Wires 308 connect the wireless antennae 306 on restraining belts 304 to a MRI data processing system.

One or more cable retractors 322 (for wires 308) are arranged, for example, at the bottom end of table 314. A cable housing 324 is arranged on either side of table 314. Cable retractors 322 and cable housing 324 operate to flexibly manage connecting the wires so that, if at all, only a minimal amount of wire is exposed in a manner that can pose a burn risk to the patient. For example, cable retractors may be spring loaded to flexibly retract amounts of excessive wire into cable housing 324 as table 314 is moved in and out of MRI gantry 326.

Figure 4:
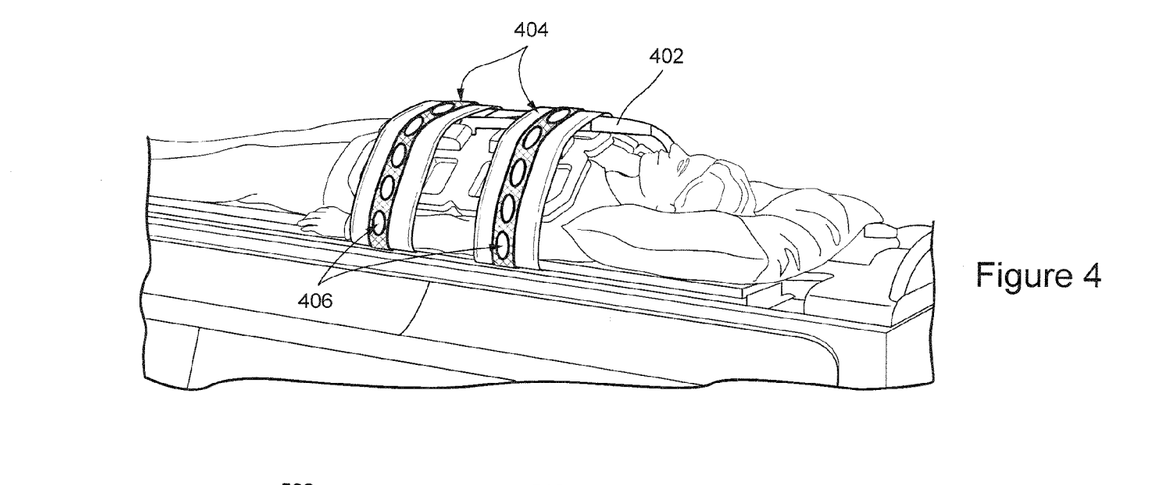
FIG. 4 illustrates a sketch of a patient secured to a patient table of a MRI system using two restraining belts that have incorporated wireless antenna for receiving MR signal data, in accordance with one or more embodiments.

FIG. 4 illustrates a sketch of a patient secured to a patient table of a MRI system using two restraining belts 404 that have incorporated wireless receivers 406 for receiving MR signal data, in accordance with one or more embodiments. As shown in FIG. 4, RF coil 402 (e.g., a "mid-body coil" in the example shown) may be held on the patient by more than one restraining belt 404. Although not shown, wireless transmit antennae are placed on the surface of RF coil 402 at least on locations under the area covered by restraining belts 404.

Figure 5:
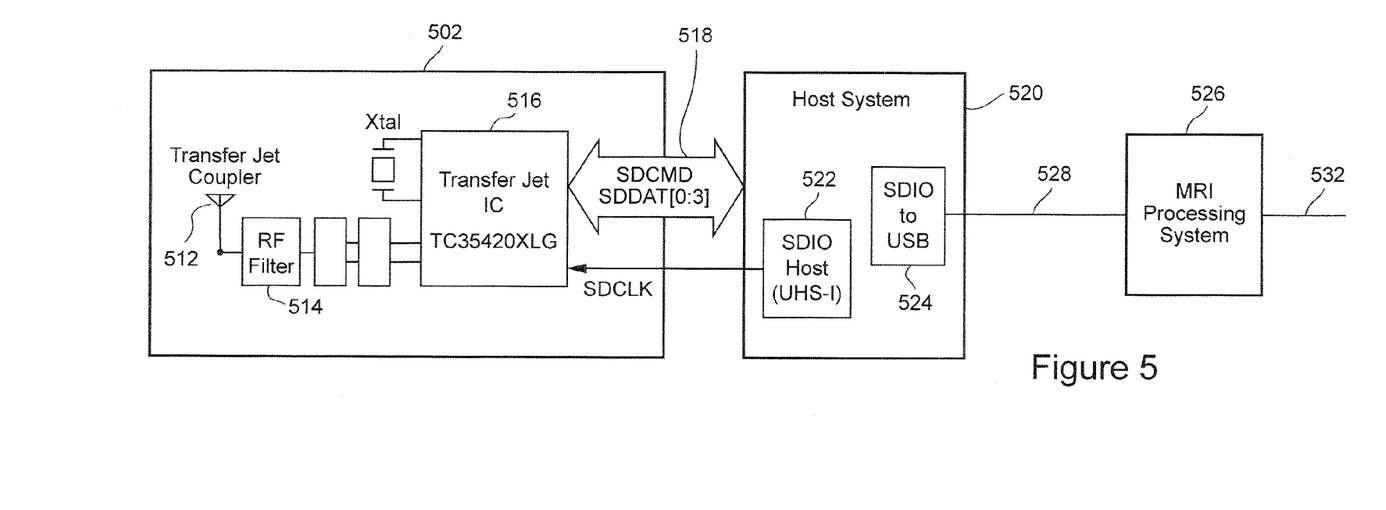
FIG. 5 illustrates an example block diagram of components organized for transferring MR data from wireless signal receivers that are incorporated to a restraining belt, in accordance with one or more embodiments.

FIG. 5 illustrates an example block diagram of components organized for transferring MR data from wireless receivers, such as wireless antennae 206, that are incorporated to a restraining belt, in accordance with one or more embodiments.

Blocks 502, 520 and 526 represent processing components that are engaged in transferring MR signals from a NFC receiver to a MRI data processing system, such as, for example, from wireless antennae in restraining belt 52 to MRI data processor 42 shown in FIG. 1.

An NFC transceiver 502, such as, for example, a Transferjet™ receiver, operates to receive MR signal data sent using an induced electric field from an NFC transmitter attached to a receive RF coil. For example, MR signal data may be received by a wireless receiver at coupler 512. After RF filtering 514, the received MR signal is transferred to a host system 520 by a controller 516 which implements the NFC communication protocol to enable the wireless receiver to establish a connection with a corresponding wireless transmitter through coupler 512. Controller 516 converts the received data to a fast data transfer format such as, for example, secure digital input output (SDIO).

Host system 520 operates, in collaboration with controller 516, to receive MR signal data in a parallel transfer format, such as, SDIO, and to adapt the received MR signal data to a second protocol format that is more suitable for the relatively long (compared to the short distance from the receiver to the host system) transmission to reach the MRI data processor. In the example shown, an SDIO host 522 establishes communication and communicates over SDIO interface 518 with the receiver to receive MR signals in SDIO format. Based upon the transfer rate of interface 518 (e.g., bus speed of 400 Mbps) an individual cable may be required for each coupling of a TransferJet™ transmitter/receiver pair. Another component of host system 520, a SDIO to universal serial bus (USB) processor 524, adapts the received SDIO data stream to USB format, which is serial and more amenable for the distance from the coils to the MRI data processor and/or to reduce the number of cables required. Host system 520 is placed closer to NFC protocol processor 516, than to MRI processing system 526. In one embodiment, host system 520 may be positioned on the restraining belt with the wireless receivers. In another embodiment, host system 520 is positioned on the patient table, for example, at a location close to where the corresponding restraining belt attaches. The MR signal data in USB format is then transferred, over interface 528 to the MRI processing system 526 to be processed into diagnostic images. The diagnostic images are then transferred over another interface 532 to a display or other output device.

Figure 6:
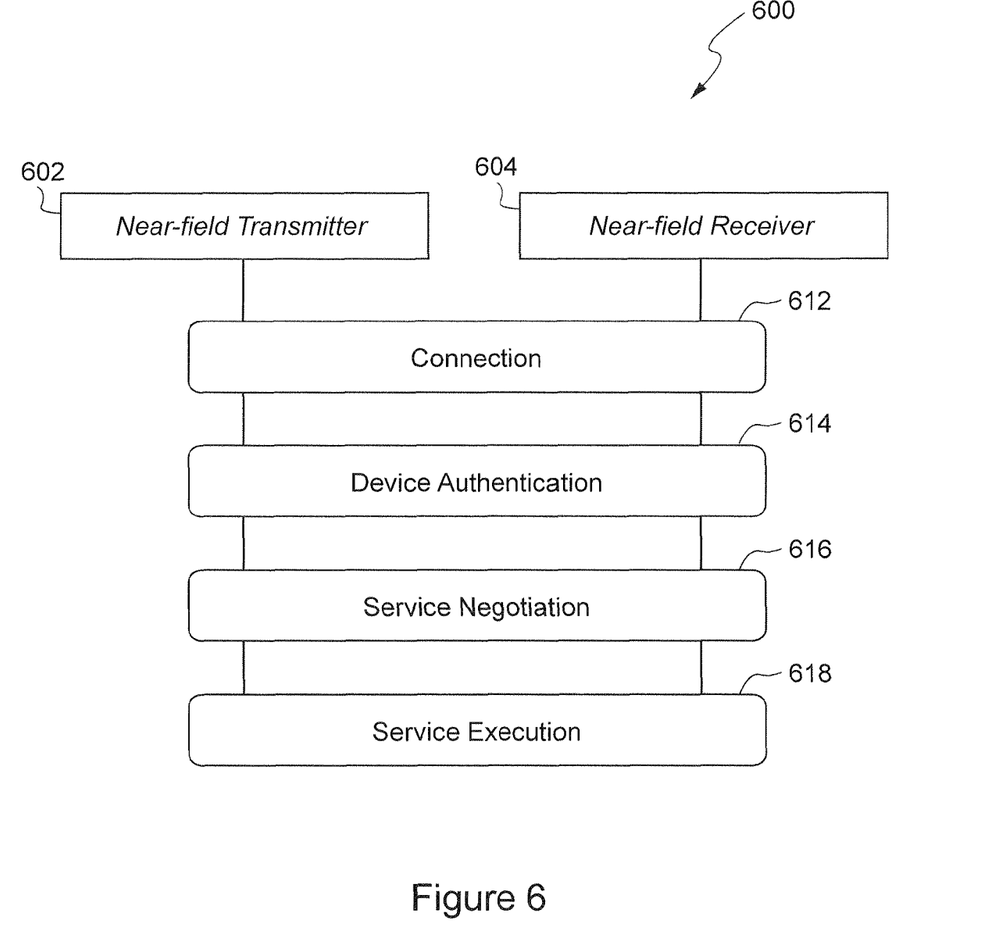
FIG. 6 illustrates protocol components that may be used in establishing a connection between a wireless signal transmitter and receiver in order to transfer data corresponding to MR signals, in accordance with one or more embodiments.

FIG. 6 illustrates protocol components 600 that may be used in establishing a connection between a wireless transmitter and a receiver in order to transfer MR signal data, in accordance with one or more embodiments. For example, FIG. 6 may describe a connection between a wireless transmitter and a wireless receiver in accordance with the TransferJet™ protocol. FIG. 6 is adapted from a corresponding diagram (FIG. 4-4) of the TransferJet™ Overview: Concept and Technology, Rev 1.1., February 2010, published by the TransferJet™ Consortium, which is hereby incorporated by reference in its entirety.

Communication is established between a NFC communication transmitter 602, such as, for example, a transmitter 220 shown in FIG. 2B, and a NFC communication receiver 604, such as, for example, a receiver 206 also shown in FIG. 2B.

The TransferJet™ protocol specifies a physical layer and a connection layer at which two TransferJet™ devices, such as, receiver 206 and transmitter 220 discussed above, communicate. In addition to the physical layer and connection layer, TransferJet™ also describes a protocol conversion layer, which corresponds to FIG. 6, which provides the necessary control functions to enable basic communications with the upper layer (e.g., application(s) through which MRI data processor 42 controls the acquisition of MR signals) as well as the adapter functions to map the lower layer to the upper applications and system interfaces. The protocol controller enables common services, such as initialization and basic communications (connection setup, connection release, and device authentication) to the higher layers. In an example MRI system, the TransferJet™ protocol, including the protocol controller, may be implemented by a TranferJet™ processor 516 included with an NFC receiver disposed on a restraining belt. A second TransferJet™ processor may be included with an NFC wireless transmitter with which the NFC receiver establishes a connection.

In order to establish communication, the transmitter 602 and receiver 604 may implement several protocol stages, such as, for example, a connection stage 612, an authentication stage 614, a service negotiation stage 616, and a service execution stage 618. Communication is established as a point-to-point connection between the paired receive controller and the transmit controller.

The connection stage enables, for example, to establish a connection between a transmitter 220 and a receiver 206 that is in communication range with the transmitter. This stage may also include selectively establishing a communication between a transmitter and receiver pair that is closest and/or most capable of reliably communicating with each other, in the event that plural pairings are possible. For example, in embodiments in which the layout density of wireless receivers on the restraining belt exceeds that of the wireless transmitters on the coil, more than one receiver may be within NFC communication range with a particular transmitter. The connection establishment may operate to select one of the wireless receivers as the selected receiver to be paired with the transmitter. The selection may be based upon the distance and/or signal strength between the transmitter and the respective receivers.

The authentication stage 614 provides for mutually authenticating the transmitter and receiver. In some embodiments, this stage may be curtailed or bypassed, for example, because the set of transmitters and the set of receivers are generally unchanging for a particular MRI system.

The service negotiation 616 and service execution 618 stages provide for the receiver and transmitter, upon a connection being established and being authenticated, to start and execute an application service. For example, the application service may be directed to initiating processes at the transmitter and the receiver in order that the MR data is received from the RF coil and transmitted to MRI data processing. In example embodiments, a host system (e.g., host system 520) may be an application service and include operations such as providing a reference signal to connected RF coils, initiate MR signal data receiving, and initiate the automatic establishing of connections between corresponding NFC transmit and receive pairs.

Figure 7:
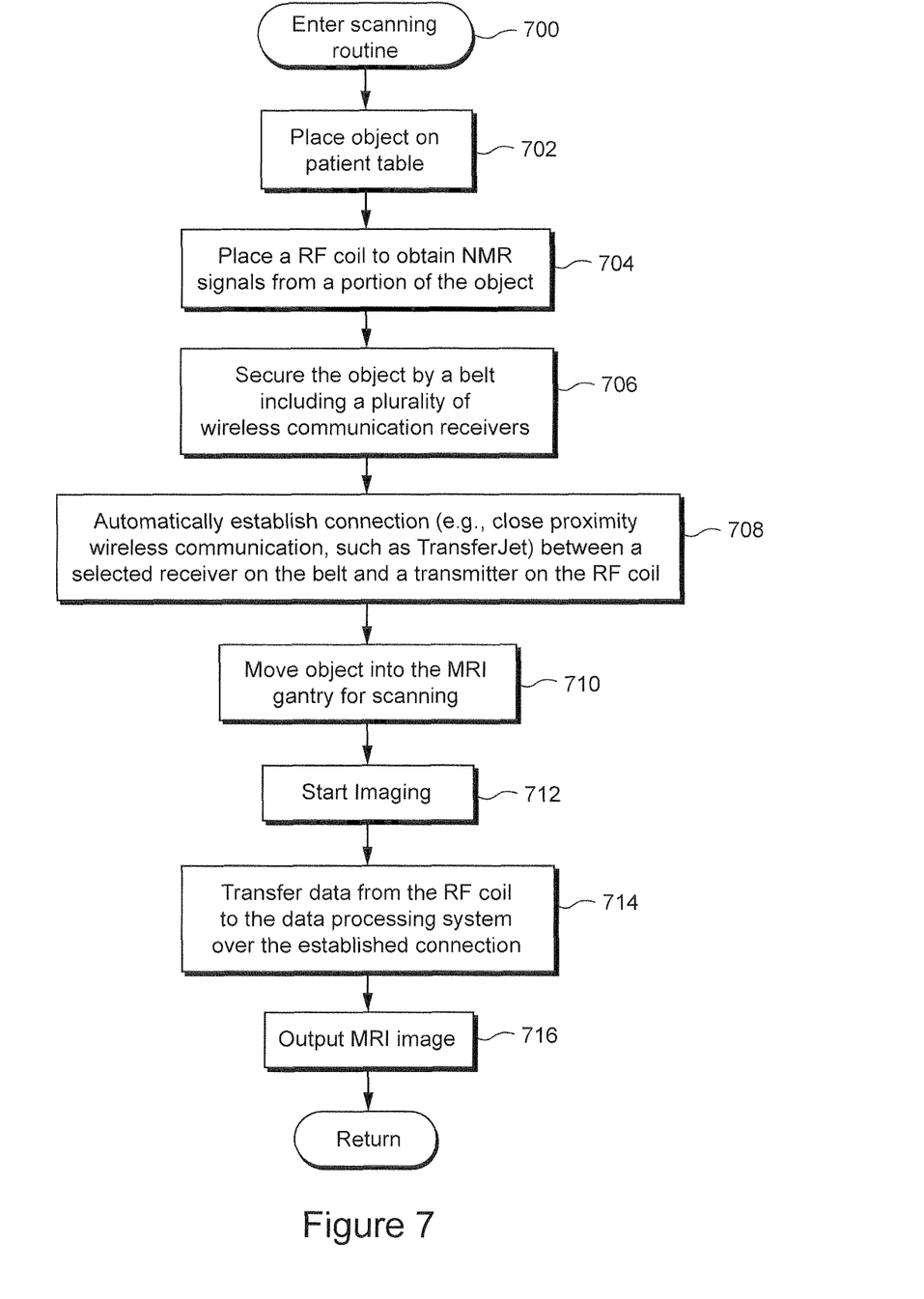
FIG. 7 illustrates a flowchart of a method for MRI scanning in accordance with one or more embodiments.

FIG. 7 illustrates a flowchart of a method 700 for MRI scanning in accordance with one or more embodiments. For example, method 700 indicates a flow of events performed in obtaining an MRI scan of a patient using an MRI system adapted to transmit MR signal data from RF coils to the MRI data processing system over a communication path that includes an NFC connection between a wireless transmitter disposed on a RF coil that receives the MR signals and a wireless receiver disposed on a restraining belt attached to the patient table of the MRI system.

At operation 702, the patient (e.g., object) is positioned on the patient table of the MRI system. As discussed above, the positioning of the object may be part of a scanning preparatory process.

At operation 704, a RF coil, such as an RF coil 19, is placed at a selected location in relation to the object. The RF coil, as discussed above, is configured to receive MR signals, and includes at least one wireless antenna to transmit the received MR signals using NFC. In an example embodiment, the RF coil and wireless transmit antenna is configured as described in relation to FIGS. 2A-B. In some embodiments, RF coil 19 may, in addition to receiving MR signals, also transmit RF excitation pulses.

At operation 706, the RF coil is secured to the object by a restraining belt that runs from one side of the patient table to the other. The restraining belt is configured with a plurality of wireless receive antennae to receive MR signal data transmitted by a wireless transmit antenna disposed on a RF coil. Example restraining belts, including restraining belts, are described in relation to FIGS. 2A-B.

At operation 708, a connection is established between at least one wireless receiver on the restraining belt and at least one transmitter on the coil. The connection may be established automatically. For example, the system automatically selects a pairing of a receiver and transmitter from a plurality of available pairing possibilities. Example protocol processing for establishing an example NFC connection between a receiver transmitter pair is described above in relation to FIG. 6. The established connection may be indicated to the operator by turning on a (light emitting diode) LED or other type of indicator on the RF coil, on the restraining belt, and/or in the display on the magnet gantry.

At operation 710, the object is moved into the MRI gantry for scanning. For example, the patient table is moved into the gantry, with the patient not being moved in relation to the patient table. Likewise, the RF coil and the restraining belt which secures the object to patient table may have no movement in relation to each other.

At operation 712, MR imaging is started.

At operation 714, MR signal data is transferred from the RF coil to the MRI data processor over the connection established during operation 708. The transfer of MR signal data is further described below in relation to FIG. 8.

At operation 716, a MRI image is constructed based upon the MR data received. The image may then be displayed and/or stored.

Figure 8:
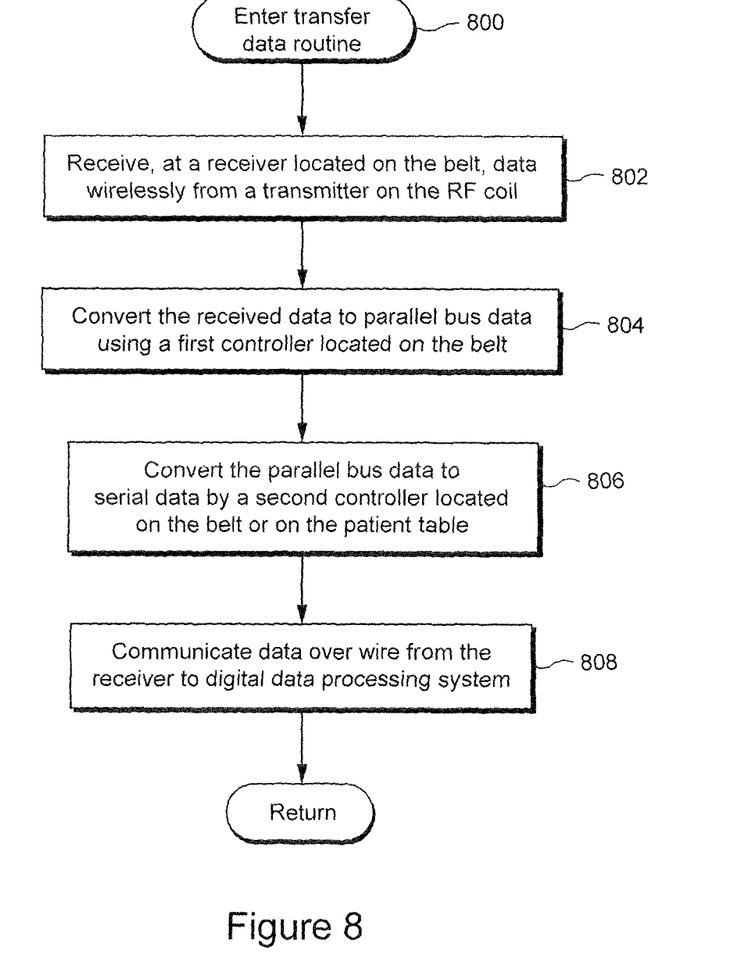
FIG. 8 illustrates a flowchart of a method for transferring information acquired from an MRI scanning to a data processing system, in accordance with one or more embodiments.

FIG. 8 illustrates a flowchart of a method 800 for transferring MR signal data to a data processing system, in accordance with one or more embodiments. According to an embodiment, method 800 may be used in performing operation 714 described above.

At operation 802, MR signal data is received at a receiver of the restraining belt. The MR signal data that is received is transmitted by a transmitter attached to a receive RF coil. The MR data is transmitted over a NFC connection formed between a receiver and transmitter. An exemplary NFC connection may be formed in accordance with the TransferJet™ protocol discussed above.

At operation 804, a NFC protocol processor (e.g., controller 516 in FIG. 5) converts the MR signal data that is received over the NFC connection into a parallel data format, such as, for example, SDIO. The NFC protocol processor may be located on the restraining belt.

At operation 806, a second processor (e.g., host system 520) receives the MR signal data in parallel form and converts to a format more suitable for the relatively long distance from where the second processor is located to the MRI data processor. In an example embodiment, a serial format, such as the USB format, may be used for the transmission from the second processor to the MRI data processor.

At operation 808, the MR signal data in serial format is transmitted over wire to the MRI data processing system.

As will be appreciated, the above embodiments provide improved MR imaging where MR signal data is transmitted from a receive RF coil to the MRI data processor via a path that includes a wireless connection, where a receiver for the wireless connection is selected from a plurality of wireless signal receivers that are arranged on a restraining belt such that when the restraining belt is placed, during operation of an MRI system for imaging an object located on a patient table, over at least a portion of the object and when the receive RF coil is located between the restraining belt and the object. Consequently, patient safety, availability of coil placement choices and the efficiency of the scanning process are improved.

While certain embodiments have been described, these embodiments have been presented by way of example only and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A magnetic resonance imaging (MRI) system comprising:
    an MRI gantry including a static magnetic field coil, gradient magnetic Field coils, at least one radio frequency (RF) coil configured to transmit RF nuclear excitation pulses into an imaging volume, and at least one MRI RF receive coil configured to receive nuclear magnetic resonance (NMR) RF signals from an object located in the imaging volume;
    at least one wireless signal transmitter coupled to the at least one MRI RF receive coil;
    a patient table configured to have the object positioned thereon and moved into the MRI gantry to place the object in the imaging volume;
    at least one digital data processor configured to receive digital magnetic resonance (MR) data from said at least one MRI RF receive coil and to generate an image using the digital MR data, the digital MR data corresponding to the NMR RF signals; and
    at least one restraining belt attached to the patient table and including one or more near-field wireless signal receivers arranged such that, when the restraining belt is placed over at least a portion of the object positioned on the patient table and the at least one MRI RF receive coil is located between the restraining belt and the object, a near-field wireless connection is established between at least one of said near-field wireless signal receivers and the at least one wireless signal transmitter coupled to the at least one MRI RF receive coil, wherein the digital MR data is transmitted from the MRI RF receive coil to the one or more near-field wireless signal receivers, and wherein the at least one digital data processor is coupled to the one or more near-field wireless signal receivers.

2. The MRI system according to claim 1, wherein said at least one MRI RF receive coil includes an analog/digital converter configured to convert received NMR RF signals to the digital MRI data which can be transmitted, the analog/digital converter being configured to wirelessly receive a reference clock signal from a wireless signal transmitter carried by the restraining belt.

3. The MRI system according to claim 1, wherein the one or more near-field wireless signal receivers comprises a plurality of near-field wireless signal receivers which are arranged, in at least one area of the restraining belt, with a density higher than that of the at least one wireless signal transmitter arranged in a corresponding area of the at least one MRI receive coil.

4. The MRI system according to claim 1,
    wherein the at least one digital data processor is coupled by flexible wires to the one or more wireless signal receivers, and
    wherein the wires include a first segment configured with a separate first wire segment for each of the wireless signal receivers and a second segment comprising a serial data communication cable to carry data from the separate first wire segments serially to the at least one digital data processor after a protocol conversion.

5. The MRI system according to claim 4, further comprising a controller configured to perform the protocol conversion, the controller being positioned on the restraining belt.

6. The MRI system according to claim 4, further comprising a controller configured to perform the protocol conversion, the controller being positioned on the patient table near a point where the restraining belt attaches to the patient table.

7. The MRI system according to claim 4, further comprising first circuitry and second circuitry, at least one of which is positioned on the restraining belt, the first circuitry being configured for converting the digital MR data from a format of a near-field wireless communication (NFC) protocol between a wireless signal receiver of the one or more wireless signal receivers and a wireless signal transmitter of the at least one wireless signal transmitter into a wired parallel bus data protocol, the second circuitry being configured for converting the digital MR data from the wired parallel data bus protocol into a serial data protocol.

8. The MRI system according to claim 1,
    wherein the at least one digital data processor is coupled by flexible wires to the one or more wireless signal receivers, and
    wherein the flexible wires are routed from the restraining belt along a surface of the patient table to the at least one digital data processor.

9. The MRI system according to claim 1,
    wherein the at least one digital data processor is coupled by flexible wires to the one or more wireless signal receivers, and
    wherein the MRI system further comprises a cable retractor configured to flexibly maintain the flexible wires without excess in areas proximate to the object as the object is moved into or out of the MRI gantry.

10. The MRI system according to claim 1, wherein the MRI system is configured to automatically select one of the one or more near-field wireless signal receivers as a selected wireless signal receiver based at least in part on proximity of the selected wireless signal receiver to a wireless signal transmitter of the at least one wireless signal transmitter.

11. The MRI system according to claim 10, wherein the selected near-field wireless signal receiver and the wireless signal transmitter are configured to communicate with each other in accordance with a near field wireless communication (NFC) protocol.

12. The MRI system according to claim 1, further comprising respective ones of the one or more near-field wireless signal receivers being associated with respective control-side wireless signal transmitters located on the restraining belt, and the at least one wireless signal transmitter coupled to the MRI RF receive coil being associated with a coil-side wireless signal receiver.

13. A method for magnetic resonance imaging (MRI), comprising:

placing a restraining belt over at least a portion of an object located on a patient table in an MRI gantry;

receiving, at an MRI radio frequency (RF) receive coil, a nuclear magnetic resonance (NMR) RF signal from the object subjected to RF nuclear excitation pulses within MRI gantry which includes a static magnetic field coil, gradient magnetic field coils, at least one RF coil configured to transmit the RF nuclear excitation pulses into an imaging volume in which the object is located, and the MRI RF receive coil;

transmitting MR data corresponding to the received NMR RF signal from a wireless signal transmitter coupled to the MRI RF receive coil;

receiving the MR data by at least one wireless signal receiver of one or more wireless signal receivers arranged on a restraining belt such that when the restraining belt is placed, during operation of the MRI gantry for imaging the object located on the patient table over the at least a portion of the object, the MRI RF receive coil is located between the restraining belt and the object;

transmitting the received MR data from the at least one wireless signal receiver to at least one MR digital data processor; and generating an image at the at least one MR digital data processor using the MR data.

14. The method according to claim 13, wherein the step of transmitting MR data comprises:

converting the MR data from a first data format to data in accordance with a near-field wireless communication (NFC) protocol; and transmitting the converted data using the NFC protocol.

15. The method according to claim 14, wherein the step of receiving the MR data comprises:

receiving the converted data; and converting the received converted data to MR data in a second data format.

16. The method according to claim 15, wherein the step of transmitting the received MR data comprises:

converting MR data from the second data format to a serial data stream; and transmitting the serial data stream to the at least one MR digital data processor.

17. The method according to claim 13, wherein the step of transmitting the received MR data comprises transmitting the received MR data via flexible wires from the at least one wireless signal receiver to the at least one MR digital data processor; and wherein the method further comprises routing the wires from the restraining belt along a surface of the patient table to the at least one MR digital data processor.

18. The method according to claim 17, wherein the step of routing the wires comprises using one or more cable retractors to flexibly maintain the wires without excess in areas proximate to the object as the object is moved.

19. The method according to claim 17, wherein the step of routing the wires includes:

configuring, for each of the one or more wireless signal receivers, an individual first wire segment to carry MR data received by each of the one or more wireless signal receivers; and aggregating a plurality of the individual first wire segments to a single serial cable to carry said MR data as serial data after a protocol conversion.

20. The method according to claim 13, wherein received NMR RF signals at said at least one MRI RF receive coil are converted from analog to digital data signals which can be transmitted as said MR data, the analog to digital conversion being effected using wirelessly received reference clock signals from a wireless signal transmitter carried by the restraining belt.

* * * * *